(12) United States Patent
Carter et al.

(10) Patent No.: US 7,084,148 B2
(45) Date of Patent: Aug. 1, 2006

(54) SUBSTITUTED PYRIMIDINES AS SELECTIVE CYCLOOXYGENASE-2 INHIBITORS

(75) Inventors: Malcolm Clive Carter, Stevenage (GB); Alan Naylor, Stevenage (GB); Martin Pass, Stevenage (GB); Jeremy John Payne, Stevenage (GB); Neil Anthony Pegg, Oxford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 150 days.

(21) Appl. No.: 10/362,745

(22) PCT Filed: Aug. 31, 2001

(86) PCT No.: PCT/GB01/03935

§ 371 (c)(1),
(2), (4) Date: Jun. 25, 2003

(87) PCT Pub. No.: WO02/18374

PCT Pub. Date: Mar. 7, 2002

(65) Prior Publication Data

US 2004/0102466 A1    May 27, 2004

(30) Foreign Application Priority Data

Sep. 1, 2000 (GB) .................. 0021494.0

(51) Int. Cl.
C07D 405/12 (2006.01)
A61K 31/505 (2006.01)

(52) U.S. Cl. .................. 514/275; 544/330; 544/332

(58) Field of Classification Search ............. 544/330, 544/332; 514/275
See application file for complete search history.

(56) References Cited

U.S. PATENT DOCUMENTS

| | | | |
|---|---|---|---|
| 3,149,109 A | 9/1964 | Neustaedter et al. | |
| 3,592,895 A | 7/1971 | Hepworth et al. | |
| 5,474,995 A | 12/1995 | Ducharme et al. | 514/241 |
| 5,760,068 A | 6/1998 | Talley et al. | 514/403 |
| 5,972,986 A | 10/1999 | Seibert et al. | 514/406 |
| 6,153,619 A | 11/2000 | Wood et al. | |
| 6,306,866 B1 | 10/2001 | Wood et al. | |
| 6,313,072 B1 | 11/2001 | Scheiblich et al. | |
| 6,780,869 B1 | 8/2004 | Green et al. | |
| 6,780,870 B1 | 8/2004 | Carter et al. | 514/275 |
| 2003/0013717 A1 | 1/2003 | Mangel et al. | 514/248 |

FOREIGN PATENT DOCUMENTS

| | | |
|---|---|---|
| DE | 19909541 | 3/1999 |
| JP | 9241161 | 9/1997 |
| WO | WO 9607641 | 3/1996 |
| WO | WO 96 24585 | 8/1996 |
| WO | WO 96 41625 | 12/1996 |
| WO | WO 96 41645 | 12/1996 |
| WO | WO 98/03484 | 1/1998 |
| WO | WO 98 16227 | 4/1998 |
| WO | WO 98/24782 | 6/1998 |
| WO | WO 99 01439 | 1/1999 |
| WO | WO 01/38311 | 5/2001 |
| WO | WO 01/58881 | 8/2001 |
| WO | WO 02/18374 | 3/2002 |
| WO | WO 02/096427 | 12/2002 |
| WO | WO 02/096885 | 12/2002 |
| WO | WO 02/096886 | 12/2002 |

OTHER PUBLICATIONS

Naesdal et al., PubMed Abstract (Eur J Gastroenterol Hepatol 13(12):1401-6), Dec. 2001.*
Simone, JV., et al. Oncology: Introduction, Cecil Textbook of Medicine, 20th Edition, vol. 1, pp. 1004-1010, 1996.

(Continued)

*Primary Examiner*—Deepak Rao
(74) *Attorney, Agent, or Firm*—J. Scott Young

(57) ABSTRACT

A compound of formula (I):

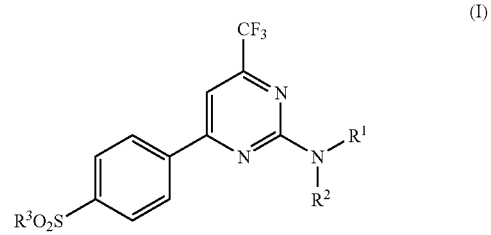

and pharmaceutically acceptable derivatives thereof, wherein $R^1$ is H or $C_{1-6}$alkyl; $R^2$ is

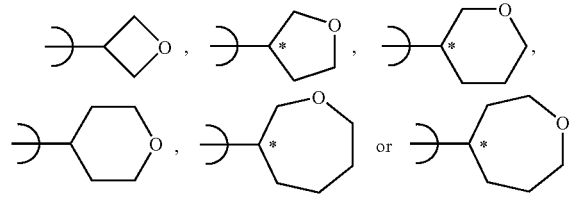

wherein

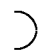

defines the point of attachment of the ring; and $R^3$ is $C_{1-6}$alkyl or $NH_2$. Compounds of formula (I) are potent and selective inhibitors of COX-2 and are of use in the treatment of pain, fever, inflammation of a variety of conditions and diseases.

23 Claims, No Drawings

OTHER PUBLICATIONS

Layzer, R.B., et al. Degenerative Diseases of the Nervous System, Cecil Textbook of Medicine, 20th Edition, vol. 2, pp. 2050-2057, 1996.

Damasio, A.R., et al. Alzheimer's Disease and Related Dementias, Cecil Textbook of Medicine, vol. 2, pp. 1992-1996, 1996.

Freston, J.W., et al. Rationalizing Cyclooxygenase (COX) Inhibition for Maximal Efficacy and Minimal Adverse Events + Abstract, Am. J. Med. 107(6A):78S-88S; Discussion 89S), Dec. 1999.

Naesdal, J. et al. "Gastro-Duodenal Protection in an Era of Cyclo-Oxygenase-2-Selective Nonsteroidal Anti-inflammatory Drugs." PubMed Abstract, Eur J Gastroenterol Hepatol. 13(12):1401-1406, Dec. 2001.

Douglas, R.G., Jr. Introduction to Viral Diseases: Cecil Textbook of Medicine, 20th Edition, vol. 2, pp. 1739-1747, 1996.

* cited by examiner

SUBSTITUTED PYRIMIDINES AS SELECTIVE CYCLOOXYGENASE-2 INHIBITORS

CROSS-REFERENCES TO RELATED APPLICATIONS

This application is a Rule 371 Application of PCT Application No. GB01/03935, filed 31 August 2001, which claims priority to GB Application Serial No. 0021494.0, filed 1 September 2000.

BACKGROUND OF THE INVENTION

This invention relates to pyrimidine derivatives, to processes for their preparation, to pharmaceutical compositions containing them and to their use in medicine.

The enzyme cyclooxygenase (COX) has recently been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is largely responsible for the important physiological functions such as maintenance of gastrointestinal integrity and renal blood flow. In contrast the inducible form, COX-2, is believed to be largely responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyreuc and analgesic properties, without the potential side effects associated with inhibition of COX-1. We have now found a novel group of compounds which are both potent and selective inhibitors of COX-2.

The invention thus provides the compounds of formula (I)

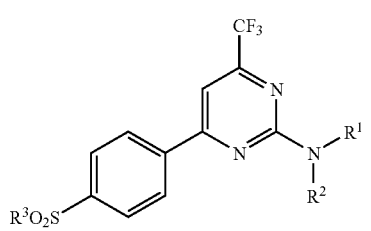

(I)

and pharmaceutically acceptable derivatives thereof, in which:
$R^1$ is H or $C_{1-6}$alkyl;
$R^2$ is

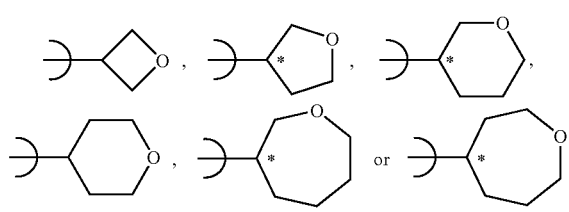

where

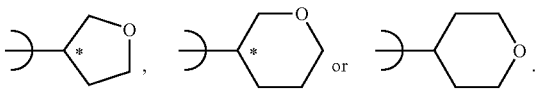

defines the point of attachment of the ring; and
$R^3$ is $C_{1-6}$alkyl or $NH_2$.

By pharmaceutically acceptable derivative is meant any pharmaceutically acceptable salt, solvate, ester or amide, or salt or solvate of such ester or amide, of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds. Of particular interest as such derivatives are compounds modified at the benzenesulphonamide function to provide metabolically labile benzenesulphonamides. Acylated benzenesulphonamide derivatives are of especial interest.

It will be appreciated by those skilled in the art that the pharmaceutically acceptable derivatives of the compounds of formula (I) may be derivatised at more than one position.

It will be further appreciated by those skilled in the art that benzenesulphonamide derivatives of formula (I) may be useful as intermediates in the preparation of compounds of formula (I), or as pharmaceutically acceptable derivatives of formula (I), or both.

It will be appreciated that, for pharmaceutical use, the salts referred to above will be the physiologically acceptable salts, but other salts may find use, for example in the preparation of compounds of formula (I) and the physiologically acceptable salts thereof.

Suitable pharmaceutically acceptable salts include: acid addition salts formed with inorganic or organic acids, preferably inorganic acids, e.g. hydrochlorides, hydrobromides and sulphates; and alkali metal salts, formed from addition of alkali metal bases, such as alkali metal hydroxides, e.g. sodium salts.

The term halogen is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

It is to be understood that the present invention encompasses all isomers of the compounds of formula (I) and their pharmaceutically acceptable derivatives, including all geometric, tautomeric and optical forms, and mixtures thereof (e.g. racemic mixtures). In particular, when the ring $R^2$ lacks a plane of symmetry the compounds of formula (I) contain a chiral centre, as indicated therein by the asterisk*.

In one aspect of the invention $R^1$ is H.
In another aspect of the invention $R^1$ is $C_{1-2}$alkyl.
In another aspect of the invention $R^2$ is In another aspect of the invention $R^3$ is $C_{1-6}$alkyl, such as $C_{1-3}$alkyl (e.g. methyl).

Within the invention there is provided one group of compounds of formula (I) wherein: $R^1$ is H; $R^2$ is

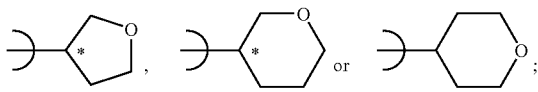

and $R^3$ is $C_{1-6}$alkyl, such as $C_{1-3}$ alkyl (e.g. methyl).

Within the invention there is provided another group of compounds of formula (I) wherein: $R^1$ is $C_{1-2}$alkyl; $R^2$ is

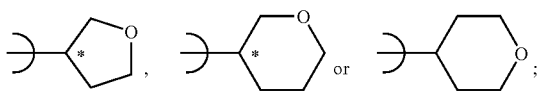

and $R^3$ is $C_{1-6}$alkyl, such as $C_{1-3}$ alkyl (e.g. methyl).

In another aspect the invention provides the following compounds:
4-[4-(methylsulfonyl)phenyl]-N-tetrahydro-2H-pyran-4-yl-6-(trifluoromethyl)pyrimidin-2-amine;
4-[4-(methylsulfonyl)phenyl]-N-methyl-N-tetrahydro-2H-pyranyl-6-(trifluoromethyl)pyrimidin-2-amine;
4-[4-(methylsulfonyl)phenyl]-N-ethyl-N-tetrahydro-2H-pyran-4-yl-6-(trifluoromethyl)pyrimidin-2-amine;

and pharmaceutically acceptable derivatives thereof.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

Compounds of the invention are potent and selective inhibitors of COX-2. This activity is illustrated by their ability to selectively inhibit COX-2 over COX-1.

In view of their selective COX-2 inhibitory activity, the compounds of the present invention are of interest for use in human and veterinary medicine, particularly in the treatment of the pain (both chronic and acute), fever and inflammation of a variety of conditions and diseases mediated by selective inhibition of COX-2. Such conditions and diseases are well known in the art and include rheumatic fever; symptoms associated with influenza or other viral infections, such as the common cold; lower back and neck pain; headache; toothache; sprains and strains; myositis; neuropathic pain (e.g. neuralgia, such as post herpetic neuralgia, trigeminal neuralgia and sympathetically maintained pain); synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

The compounds of the invention are also useful for the treatment of other conditions mediated by selective inhibition of COX-2.

For example, the compounds of the invention inhibit cellular and neoplastic transformation and metastatic tumour growth and hence are useful in the treatment of certain cancerous diseases, such as colonic cancer. The compounds of the invention are also useful in reducing the number of adenomatous colorectal polyps, and thus reduce the risk of developing colon cancer. The compounds of the invention are also useful in the treatment of cancer associated with overexpression of HER-2/neu, in particular breast cancer.

Compounds of the invention also prevent neuronal injury by inhibiting the generation of neuronal free radicals (and hence oxidative stress) and therefore are of use in the treatment of stroke; epilepsy; and epileptic seizures (including grand mal, petit mal, myoclonic epilepsy and partial seizures).

Compounds of the invention also inhibit prostanoid-induced smooth muscle contraction and hence are of use in the treatment of dysmenorrhoea and premature labour.

Compounds of the invention are also useful in the treatment of liver disease such as inflammatory liver disease, for example chronic viral hepatitis B, chronic viral hepatitis C, alcoholic liver injury, primary biliary cirrhosis, autoimmune hepatitis, nonalcoholic steatohepatitis and liver transplant rejection.

Compounds of the invention inhibit inflammatory processes and therefore are of use in the treatment of asthma, allergic rhinitis and respiratory distress syndrome; gastrointestinal conditions such as inflammatory bowel disease, Crohn's disease, gastritis, irritable bowel syndrome and ulcerative colitis; and the inflammation in such diseases as vascular disease, migraine, periarteritis nodosa, thyroiditis, aplastic anaemia, Hodgkin's disease, scleroderma, type I diabetes, myasthenia gravis, multiple sclerosis, sorcoidosis, nephrotic syndrome, Bechet's syndrome, polymyositis, gingivitis, conjunctivitis and myocardial ischemia.

Compounds of the invention are also useful in the treatment of ophthalmic diseases such as retinitis, retinopathies, uveitis and of acute injury to the eye tissue.

Compounds of the invention are also useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment.

Compounds of the invention are also useful in the treatment of disorders ameliorated by a gastroprokinetic agent. Disorders ameliorated by gastroprokinetic agents include ileus, for example post-operative ileus and ileus during sepsis; gastroesophageal reflux disease (GORD, or its synonym GERD); gastroparesis, such as diabetic gastroparesis; and other functional bowel disorders, such as non-ulcerative dyspepsia (NUD) and non-cardiac chest pain (NCCP).

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by selective inhibition of COX-2.

According to a further aspect of the invention, we provide a method of treating a human or animal subject suffering from a condition which is mediated by selective inhibition of COX-2 which comprises administering to said subject an effective amount of a compound of formula (I) or a pharmaceutically acceptable derivative.

According to a further aspect of the invention, we provide a method of treating a human or animal subject suffering from an inflammatory disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by selective inhibition of COX-2.

According to another aspect of the invention, we provide the use of a compound of formula (I) or a pharmaceutically acceptable derivative thereof for the manufacture of a therapeutic agent for the treatment of an inflammatory disorder.

It is to be understood that reference to treatment includes both treatment of established symptoms and prophylactic treatment, unless explicitly stated otherwise.

It will be appreciated that the compounds of the invention may advantageously be used in conjunction with one or more other therapeutic agents. Examples of suitable agents for adjunctive therapy include pain relievers such as a $5HT_1$ agonist (e.g. sumatriptan), an adenosine A1 agonist, an EP ligand (e.g. an EP4 antagonist), a glycine antagonist, a sodium channel inhibitor (e.g. lamotrigine), a substance P antagonist (e.g. an $NK_1$ antagonist), cannabinoids, acetaminophen or phenacetin; a matrix metalloproteinase inhibitor; a nitric oxide synthase (NOS) inhibitor (e.g. an iNOS or an nNOS inhibitor); an inhibitor of the release, or action, of tumour necrosis factor α; an antibody therapy (e.g. a monoclonal antibody therapy); a stimulant, including caffeine; an $H_2$-antagonist, such as ranitidine; a proton pump inhibitor, such as omeprazole; an antacid, such as aluminium or magnesium hydroxide; an antiflatulent, such as simethicone; a decongestant, such as phenylephrine, phenylpropanolamine, pseudoephedrine, oxymetazoline, epinephrine, naphazoline, xylometazoline, propylhexedrine, or levo-desoxyephedrine; an antitussive, such as codeine, hydrocodone, carmiphen, carbetapentane, or dextramethorphan; a diuretic; or a sedating or non-sedating antihistamine. It is to be understood that the present invention covers the use of a compound of formula (I) or a pharmaceutically acceptable derivative thereof in combination with one or more other therapeutic agents.

Further examples of suitable agents for adjunctive therapy include a 5-lipoxygenase inhibitor, a leukotriene receptor antagonist; a DMARD (e.g. methotrexate); gabapentin and related compounds; a tricyclic antidepressant (e.g. amitryptilline); a neurone stabilising antiepileptic drug; a monoaminergic uptake inhibitor (e.g. venlafaxine); an antiviral agent, such as a nucleoside inhibitor (e.g. lamivudine) or an immune system modulator (e.g. interferon); an opiod analgesic or a local anaesthetic.

The compounds of formula (I) and their pharmaceutically acceptable derivatives are conveniently administered in the form of pharmaceutical compositions. Thus, in another aspect of the invention, we provide a pharmaceutical composition comprising a compound of formula (I) or a pharmaceutically acceptable derivative thereof adapted for use in human or veterinary medicine. Such compositions may conveniently be presented for use in conventional manner in admixture with one or more physiologically acceptable carriers or excipients.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

As stated above, the compounds of the invention may also be used in combination with other therapeutic agents. The invention thus provides, in a further aspect, a combination comprising a compound of formula (I) or a pharmaceutically acceptable derivative thereof together with a further therapeutic agent.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A proposed daily dosage of a compound of formula (I) for the treatment of man is 0.01 mg/kg to 500 mg/kg, such as 0.05 mg/kg to 100 mg/kg, e.g. 0.1 mg/kg to 50 mg/kg, which may be conveniently administered in 1 to 4 doses. The precise dose employed will depend on the age and condition of the patient and on the route of administration. Thus, for example, a daily dose of 0.25 mg/kg to 10 mg/kg may be suitable for systemic administration.

Compounds of formula (I) and pharmaceutically acceptable derivatives thereof may be prepared by any method known in the art for the preparation of compounds of analogous structure.

Compounds of formula (I) and pharmaceutically acceptable derivatives thereof may be prepared by a process which comprises:

(A), reacting an amine $HNR^1R^2$ of formula (II) or a protected derivative thereof with a compound of formula (III)

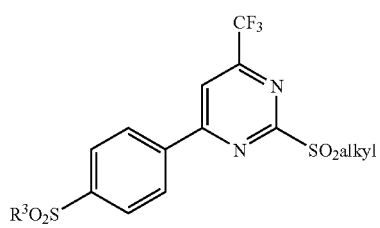

(III)

or a protected derivative thereof; or (B), interconverting of a compound of formula (I) into another compound of formula (I); in particular, for a compound of formula (I) in which $R^1$ is H, alkylation thereof to give a compound of formula (I) in which $R^1$ is $C_{1-6}$alkyl; and/or (C), deprotecting a protected derivative of compound of formula (I); and optionally converting compounds of formula (I) prepared by any one of processes (A) to (C) into pharmaceutically acceptable derivatives thereof.

Suitable methods for the preparation of compounds of formula (I) and pharmaceutically acceptable derivatives thereof are disclosed in Scheme 1 that follows. In Scheme 1, $R^1$ to $R^3$ are as defined in formula (I) above unless otherwise stated; Hal is a halogen, such as Cl or Br; MTBE is methyl t-butyl ether; and alkyl is a straight or branched chain alkyl group, for example a methyl, ethyl, n-propyl, i-propyl, n-butyl, s-butyl or t-butyl group.

Referring to Scheme 1, the treatment of compounds of formula (III) with an amine of formula (II) is conveniently carried out in a suitable solvent, such as acetonitrile or N-methylpyrrolidone, and at elevated temperature (e.g. from about 50° C. to reflux). An excess of the amine may be used in place of the solvent.

Conveniently, the boronic acid coupling shown in Scheme 1 is carried out in a solvent, such as an ether (e.g. 1,2-dimethoxyethane); in the presence of a base, such as an inorganic base (e.g. sodium carbonate); and employing a palladium catalyst, such as tetrakis(triphenylphosphine)palladium(0).

Conveniently the oxidation shown in Scheme 1 is effected using a monopersulfate compound, such as potassium peroxymonosulfate (known as Oxone™) and the reaction is carried out in a solvent, such as an aqueous alcohol, (e.g. aqueous methanol), and at between −78° C. and ambient temperature.

Referring to Scheme 1, the cyclisation of diones of formula (VI) to give the corresponding pyrimidines of formula (IV) is conveniently carried out employing a thiouronium salt such as a 2-methyl-2-thiopseudourea sulfate and under reflux.

It will be appreciated by those skilled in the art that certain of the procedures described in Scheme 1 for the preparation of compounds of formula (I) or intermediates thereto may not be applicable to some of the possible substituents.

Scheme 1

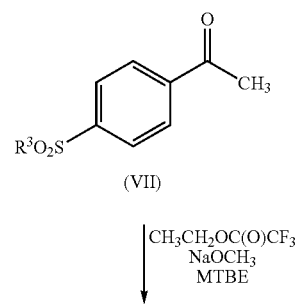

(VII)

$CH_3CH_2OC(O)CF_3$
$NaOCH_3$
MTBE

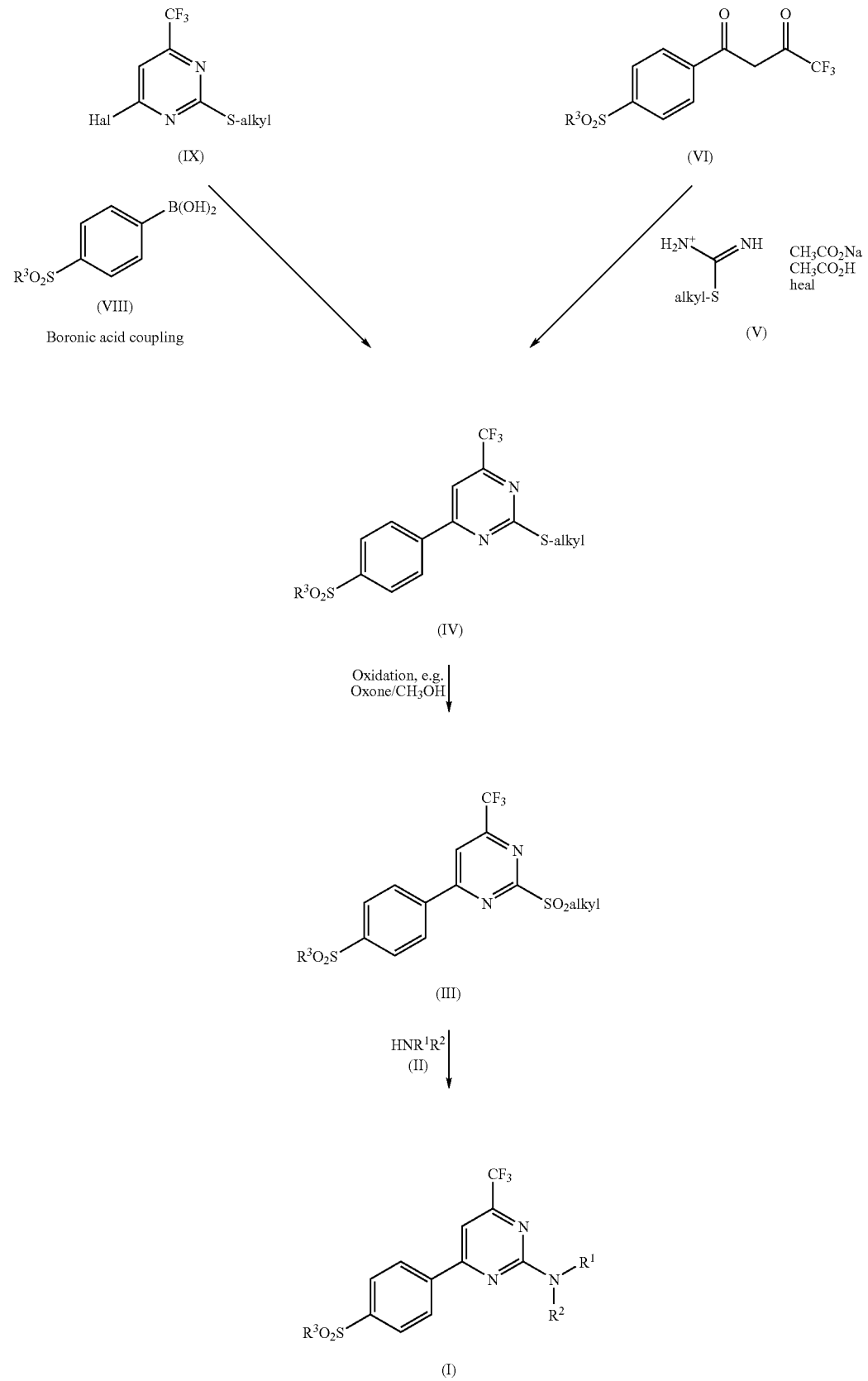

It will be further appreciated by those skilled in the art that it may be necessary or desirable to carry out the transformations described in Scheme 1 in a different order from that described, or to modify one or more of the transformations, to provide the desired compound of formula (I).

In one variation of Scheme 1, compounds of formula (III) wherein $R^3$ is $C_{1-6}$alkyl may be prepared by oxidising a disulphide of formula (IV)A:

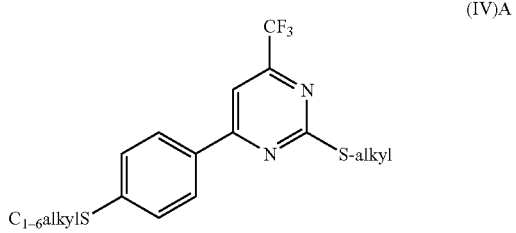

(IV)A under oxidation conditions described hereinabove. Disulphides of formula (IV)A may be prepared according to the general procedures of Scheme 1 by employing sulphide derivatives in place of the corresponding alkylsulphonyl compounds of formulae (VII) and (VIII).

It will be appreciated by those skilled in the art that compounds of formula (I) may be prepared by interconversion, utilising other compounds of formula (I) as precursors. Suitable interconversions, such as alkylations, are well known to those skilled in the art and are described in many standard organic chemistry texts, such as 'Advanced Organic Chemistry' by Jerry March, fourth edition (Wiley, 1992), incorporated herein by reference. For example, compounds of formula (I) wherein $R^1$ is $C_{1-6}$alkyl may be prepared by alkylating the corresponding compound of formula (I) wherein $R^1$ is H.

Acylation of compounds of formula (I) wherein $R^3$ is $NH_2$ to provide corresponding acylated benzenesulphonamide derivatives may be carried out by conventional means, for example by employing conventional acylating agents such as those described in 'Advanced Organic Chemistry', pp 417–424.

As will be appreciated by those skilled in the art it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See, for example, those described in 'Protective Groups in Organic Synthesis' by Theodora W Green and Peter G M Wuts, second edition, (John Wiley and Sons, 1991), incorporated herein by reference, which also describes methods for the removal of such groups.

Amines of formula (II) are either known compounds or may be prepared by literature methods, such as those described in 'Comprehensive Organic Transformations: a guide to functional group preparations' by Richard Larock (VCH, 1989), incorporated herein by reference.

Thiouronium salts of formula (V) are either known compounds or may be prepared by literature methods, such as those described in A H Owens et al., Eur J Med Chem, 1988, 23(3), 295–300, incorporated herein by reference Acetophenones of formula (VII) are either known compounds or may be prepared by conventional chemistry.

Boronic acids of formula (VII) or derivatives thereof are either known compounds or may be prepared by literature methods, such as those described in EPA publication No. 533268; or R Miyaura et al, J Org Chem, 1995, 60, 7508–7510; each incorporated herein by reference.

4-Halo-6-trifluoromethylpyrimidines of formula (IX) are either known compounds or may be prepared by literature methods, such as those described in Japanese Patent no. 42014952 (Chem Abs ref CAN 68:105224), incorporated herein by reference.

Certain intermediates described above are novel compounds, and it is to be understood that all novel intermediates herein form further aspects of the present invention. Conveniently, compounds of the invention are isolated following work-up in the form of the free base. Pharmaceutically acceptable acid addition salts of the compounds of the invention may be prepared using conventional means.

Solvates (e.g. hydrates) of a compound of the invention may be formed during the work-up procedure of one of the aforementioned process steps.

The Intermediates and Examples that follow illustrate the invention but do not limit the invention in any way. All temperatures are in ° C. Flash column chromatography was carried out using Merck 9385 silica. Solid Phase Extraction (SPE) chromatography was carried out using Varian Mega Bond Elut (Si) cartridges (Anachem) under 15 mmHg vacuum with stepped gradient elution. Thin layer chromatography (Tlc) was carried out on silica plates. Autopurification was performed using a system comprising a Supelco ABZ+column, 2xGilson 305 single piston pumps, a Gilson 155 Dual Wavelength UV detector, a Gilson 233XL autosampler/fraction collector, a Gilson 506c interface unit and a computer system operated via Gilson UniPoint software. The mobile phase was varied with time according to the following table wherein solvent A is 0.1% aqueous formic acid and solvent B is 95% acetonitrile.

| Time (min) | % A | % B |
|---|---|---|
| 0.01 | 70 | 30 |
| 1.45 | 70 | 30 |
| 20 | 40 | 60 |
| 30 | 40 | 60 |
| 30.02 | 0 | 100 |
| 54 | 0 | 100 |
| 54.02 | 70 | 30 |
| 56 | 70 | 30 |

In addition to those already defined, the following abbreviations are used: Me, methyl; Ac, acyl; DMSO, dimethylsulphoxide; TFA, trifluoroacetic acid; DME, dimethoxyethane; THF, tetrahydrofuran; DCM, dichloromethane; MTBE, methyl t-butyl ether; and NMP, N-methylpyrrolidone.

Intermediate 1

4,4,4-Trifluoro-1-[4-(methylthio)phenyl]butane-1,3-dione

To a solution of ethyl trifluoroacetate (7.95 ml, 1.1 eq) in MTBE (125 ml) was added dropwise 25% sodium methoxide in methanol (16 ml, 1.2 eq). 4-Methylthioacetophenone (Aldrich, 10 g, 0.06 mol) was added portionwise and the mixture stirred at ambient temperature overnight. 2N Hydrochloric acid (40 ml) was added cautiously and the organic phase separated, washed with brine and dried ($Na_2SO_4$) to give an orange solid. The orange solid was recrystallised from hot isopropanol to give the title compound as a yellow crystalline solid (11.25 g, 71%).

MH– 261

Intermediate 2

2-(Methylthio)-4-[4-(methylthio)phenyl]-6-(trifluoromethyl)pyrimidine

To a mixture of 4,4,4-trifluoro-1-[4-(methylthio)phenyl] butane-1,3-dione (5 g) and 2-methyl-2-thiopseudourea sulfate (5.1 g, 0.98 eq) in acetic acid (100 ml) was added sodium acetate (3 g, 2 eq) and heated under reflux for 8 h. The mixture was concentrated in vacuo and water (100 ml) added to give a solid, which was isolated by filtration to give the title compound as a yellow solid (5.8 g, quantitative).

MH+ 317

Intermediate 3

2-(Methylthio)-4-[4(methylthio)phenyl]-6-(trifluoromethyl) pyrimidine

A mixture of 4-chloro-2-methylthio-6-(trifluoromethyl) pyrimidine (ButtPark Ltd, 2.86 g, 14.55 mmol), 4-(methylthio)phenylboronic acid (Aldrich, 2.83 g, 1.1 eq), tetrakistriphenylphosphine palladium (0) (0.2 g) and sodium carbonate (4.04 g, 2.6 eq) in DME (200 ml) and water (100 ml) was heated under reflux with stirring under $N_2$ for 24 h. The reaction mixture was concentrated in vacuo and the resultant mixture partitioned between ethyl acetate and water. The organic phase was separated, washed with water, dried ($Na_2SO_4$) and concentrated in vacuo to a purple solid. Purification by flash column chromatography with cyclohexane:ethyl acetate as (6:1) as eluant gave the title compound as a yellow crystalline solid (3.869, 84%).

MH+ 317

TLC $SiO_2$ cyclohexane:ethyl acetate (3:1) Rf 0.75 $uv_{254}$

Intermediate 4

2-(Methylsulfonyl)-4-[4-(methylsulfonyl)phenyl]-6-(trifluoromethyl)Pydmidine

To a solution of 2-(methylthio)-4-[4-(methylthio)phenyl]-6-(trifluoromethyl) pyrimidine (5.78 g) in MeOH (500 ml) was added a solution of OXONE™ (Aldrich, 56.23 g, 5 eq) in water (200 ml). The mixture was stirred at ambient temperature overnight, concentrated in vacuo and the residue partitioned between water and ethyl acetate (2×100 ml). The combined organic phases were dried and concentrated in vacuo to an off-white solid which was triturated with hot isopropanol to give the title compound as a white solid (5.6 g, 80%).

MH+ 381

Tlc $SiO_2$ Ethyl acetate:cyclohexane (1:1) Rf 0.45

EXAMPLE 1

4-[4-(methylsulfonyl)phenyl]-N-tetrahydro-2H-pyran-4-yl-6-(trifluoromethyl)pyrimidin-2-amine To a solution of 2-(methylsulfonyl)-4-[4-(methylsulfonyl) phenyl]-6-(trifluoromethyl)pyrimidine (0.277 g, 0.73 mmol) in N-methylpyrrolidone (1.25 ml) was added tetrahydro-2H-pyran-4-amine (0.147 g, 2 eq.), the mixture was stirred for 1 hour and then water (1.25 ml) was added dropwise. This resulted in a precipitate being formed, which was collected by filtration, and dried in vacuo (0.258 g). This material was then purified by autopurification to give the title compound as a colourless solid (0.116 g, 40%).

MH+ 402

EXAMPLE 2

4-[4-(Methylsulfonyl)phenyl]-N-methyl-N-tetrahydro-2H-pyran-4-yl-6-(trifluoromethyl)pyrimidin-2-amine A solution of 4-[4-(methylsulfonyl)phenyl]-N-tetrahydro-2H-pyran-4-yl-6-(trifluoromethyl)pyrimidin-2-amine (0.05 g) in dry dimethylformamide (2 ml) was treated with sodium hydride (0.007 g, 60% in mineral oil) and the mixture stirred at ambient temperature for 30 minutes. Iodomethane (0.01 ml) was added and the mixture stirred overnight. The reaction mixture was concentrated in vacuo and the residue partitioned between dichloromethane (20 ml) and water (20 ml). The organic layer was purified by passing through a silica bond elute column and eluting with dichloromethane. Concentration of the eluent gave the title compound as a yellow solid (0.031 g).

LCMS rt=3.69 min m/z(MH+)=416

The following examples were prepared by an analogous method to that for Example 2

EXAMPLE 3

4-[4-(Methylsulfonyl)phenyl]-N-ethyl-N-tetrahydro-2H-pyran-4-yl-6-(trifluoromethyl)pyrimidin-2-amine LCMS rt=3.68 min m/z(MH+)=430

EXAMPLE 4

4-[4-(Methylsulfonyl)phenyl]-N-butyl-N-tetrahydro-2H-pyran-4-yl-6-(trifluoromethyl)pyrimidin-2-amine LCMS rt=3.82 m/z(MH+)=458

Biological Data

Inhibitory activity against human COX-1 and COX-2 was assessed in COS cells which had been stably transfected with cDNA for human COX-1 and human COX-2. 24 Hours prior to experiment, COS cells were transferred from the 175 $cm^2$ flasks in which they were grown, onto 24-well cell culture plates using the following procedure. The incubation medium (Dulbecco's modified eagles medium (DMEM) supplemented with heat-inactivated foetal calf serum (10% v/v), penicillin (100 IU/ml), streptomycin (100 µg/ml) and geneticin (600 µg/ml)) was removed from a flask of confluent cells (1 flask at confluency contains approximately $1 \times 10^7$ cells). 5 ml of phosphate buffered saline (PBS) was added to the flask to wash the cells. Having discarded the PBS, cells were then incubated with 5 ml trypsin for 5 minutes in an incubator (370). The flask was then removed from the incubator and 5 ml of fresh incubation medium was added. The contents of the flask was transferred to a 250 ml sterile container and the volume of incubation medium subsequently made up to 100 ml. 1 ml cell suspension was pipetted into each well of 4×24-well cell culture plates. The plates were then placed in an incubator (37° C., 95% air/5% $CO_2$) overnight. If more than 1 flask of cells were required, the cells from the individual flasks were combined before being dispensed into the 24-well plates.

Following the overnight incubation, the incubation medium was completely removed from the 24-well cell culture plates and replaced with 250 µl fresh DMEM (37° C.). The test compounds were made up to 250× the required test concentration in DMSO and were added to the wells in a volume of 1 µl. Plates were then mixed gently by swirling and then placed in an incubator for 1 hour (37° C., 95% air/5% $CO_2$). Following the incubation period, 10 µl of arachidonic acid (750 µM) was added to each well to give a final arachidonic acid concentration of 30 µM. Plates were then incubated for a further 10 minutes, after which the incubation medium was removed from each well of the plates and stored at −20° C., prior to determination of prostaglandin $E_2$ (PGE2) levels using enzyme immunoassay. The inhibitory potency of the test compound was expressed as an $IC_{50}$ value, which is defined as the concentration of the compound required to inhibit the PGE2 release from the cells by 50%. The selectivity ratio of inhibition of COX-1 versus COX-2 was calculated by comparing respective $IC_{50}$ values.

The following $IC_{50}$ values for inhibition of COX-2 and COX-1 were obtained for compounds of the invention:

| Example No. | COX-2: $IC_{50}$(nM) | COX-1: $IC_{50}$(nM) |
|---|---|---|
| 1 | 18 | >91,000 |
| 2 | 16.8 | 60357 |
| 3 | 24.9 | 69710 |
| 4 | 143.3 | 71815 |

The invention claimed is:

1. A compound of formula (I)

or a pharmaceutically acceptable salt or solvate thereof, in which:

$R^1$ is H or $C_{1-6}$alkyl;

$R^2$ is wherein

)

defines the point of attachment of the ring; and $R^3$ is $C_{1-6}$alkyl or $NH_2$.

2. A compound as claimed in claim 1 wherein $R^1$ is H.

3. A compound as claimed in claim 1 wherein $R^1$ is $C_{1-2}$alkyl.

4. A compound as claimed in claim 1 wherein $R^2$ is

5. A compound as claimed in claim 1 wherein $R^3$ is $C_{1-6}$alkyl.

6. A compound as claimed in claim 1 wherein $R^1$ is H; $R^2$ is and $R^3$ is methyl.

7. A compound as claimed in claim 1 wherein $R^1$ is $C_{1-2}$alkyl; $R^2$ is and $R^3$ is methyl.

8. A compound selected from:

4-[4-(methylsulfonyl)phenyl]-N-tetrahydro-2H-pyran-4-yl-6-(trifluoromethyl)pyrimidin-2-amine;

4-[4-(methylsulfonyl)phenyl]-N-methyl-N-tetrahydro-2H-pyran-4-yl-6-(trifluoromethyl)pyrimidin-2-amine;

4-[4-(methylsulfonyl)phenyl]-N-ethyl-N-tetrahydro-2H-pyran-4-yl-6-(trifluoromethyl)pyrimidin-2-amine;

or a pharmaceutically acceptable salt or solvate thereof.

9. A process for the preparation of a compound as defined in claim 1, which comprises:

(A), reacting an amine of formula $HNR^1R^2$ or a protected derivative thereof with a compound of formula (III)

or a protected derivative thereof; or (B), interconverting of a compound of formula (I) into another compound of formula (I); or (C), deprotecting a protected derivative of compound of formula (I); and optionally converting compounds of formula (I) prepared by any one of processes (A) to (C) into pharmaceutically acceptable salt or solvate thereof.

10. A pharmaceutical composition comprising a compound as defined in claim 1 in admixture with one or more physiologically acceptable carriers or excipients.

11. A method of treating a subject suffering from rhumatoid arthritis, which method comprises administering to said subject an effective COX-2 inhibiting amount of a compound according to claim 1.

12. A method of treating a subject suffering from osteoarthritis, which method comprises administering to said subject an effective COX-2 inhibiting amount of a compound according to claim 1.

13. A method of treating a subject suffering from pain, which method comprises administering to said subject an effective COX-2 inhibiting amount of a compound according to claim 1.

14. A method of treating a subject suffering from inflammation in multiple sclerosis, which method comprises administering to said subject en effective COX-2 inhibiting amount of a compound according to claim 1.

15. A method of treating a subject suffering from inflammation in migraine, which method comprises administering to said subject an effective COX-2 inhibiting amount of a compound according to claim 1.

16. The method according to claim 13 wherein said pain is lower back or neck pain.

17. The method according to claim 13 wherein said pain is neuropathic pain.

18. The method according to claim 13 wherein said pain is non-specific lower back pain.

19. The method according to claim 13 wherein said pain is post-herpetic neuralgia.

20. The method according to claim 13 wherein said subject is a human.

21. A method of treating a subject suffering from dysmenorrhoea which comprises administering to said subject an effective amount of a compound as claimed in claim 1.

22. The method according to claim 21, wherein said subject is a human.

23. A method of treating a subject suffering from arthritis which comprises administering to said subject an effective amount of a compound as defined in claim 1.

* * * * *